United States Patent
Rainen et al.

(10) Patent No.: US 6,361,505 B1
(45) Date of Patent: Mar. 26, 2002

(54) SAMPLE COLLECTION ASSEMBLY FOR COLLECTION OF A BULK AND DROP SAMPLE

(75) Inventors: Lynne C. Rainen, Maplewood; Nicholas A. Grippi, Wayne, both of NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 09/607,885

(22) Filed: Jun. 30, 2000

(51) Int. Cl.⁷ .................................................. A61B 5/00
(52) U.S. Cl. ....................... 600/577; 600/584
(58) Field of Search ................... 600/576, 577, 600/583, 584; 604/167, 256

(56) References Cited

U.S. PATENT DOCUMENTS

| 2,876,775 | A | * | 10/1959 | Barr et al. ................... 600/577 |
| 4,863,453 | A | * | 9/1989 | Berger et al. ................ 600/577 |
| 5,951,492 | A | * | 9/1999 | Douglas et al. ............. 600/584 |

* cited by examiner

Primary Examiner—Max Hindenburg
(74) Attorney, Agent, or Firm—Nanette S. Thomas (57) ABSTRACT

A sample collection assembly provides for the simultaneous collection of a bulk sample and a drop sample. The assembly includes a specimen collection container for collection of the bulk sample from an insertable probe. A drop sample substrate is positioned across an open end of the container or the closure that is in the open end of the container. The drop sample substrate is puncturable by the probe upon probe insertion. The drop sample substrate includes a drop sample retaining surface for retaining the drop sample upon withdrawal of the probe from the container.

16 Claims, 7 Drawing Sheets

SAMPLE COLLECTION ASSEMBLY FOR COLLECTION OF A BULK AND DROP SAMPLE

BACKGROUND OF THE INVENTION

1. Field of the Invention

The present invention relates to an assembly for collection of a biological sample. More particularly, the present invention relates to a sample collection assembly which permits the simultaneous collection of a bulk sample and a drop sample and which provides for coordinated tracking and identification of the sample.

2. Description of Related Art

Various biological samples, such as whole blood, urine specimen, saliva and fecal samples are commonly collected in containers and tubes for subsequent testing and analysis. Each type of sample uses a distinct collection container and associated sampling techniques. For example, with respect to the collection of blood, samples of whole blood are typically collected from a patient by venipuncture with a cannula or a needle attached to a syringe or an evacuated collection tube. A container such as a blood collection tube containing the collected sample is subsequently shipped to a laboratory where experienced personnel subject the blood sample to specific tests.

Often, it is necessary for a small amount of the collected sample to be tested separately from the bulk of the collected sample. Such tests may include PCR (polymerase chain reaction) or other gene amplification analyses. These tests are typically conducted on a drop sample, that is, a drop of the sample fluid placed on filter paper or other substrate. The drop sample may be placed on the filter paper either at the time of sample collection from the patient or subsequently from the previously obtained bulk sample. In either case, an additional step of collecting the drop sample is required. Where the drop sample is obtained directly from the patient, it requires the technician to obtain the drop sample separate from the bulk sample and also to assure that the drop sample is separately identified, ID contained and transported in a safe and efficient manner along with the coordinated identification and transport of the bulk sample. Where the drop sample is obtained from the bulk sample at the laboratory, it requires the technician to reenter the bulk specimen container to obtain the drop sample.

In both instances, the potential exists for mishandling or misidentifying the drop sample with respect to the bulk sample. Furthermore, obtaining a drop sample separately from the bulk sample also potentially poses an increased biohazard risk to the technician collecting and transporting the separate samples.

It is therefore desirable to provide a technique for obtaining a drop sample simultaneously with a bulk sample and to assure proper identification and trackability between the bulk sample and the drop sample during transport and analysis.

SUMMARY OF THE INVENTION

The present invention provides a sample collection assembly for the collection of a drop sample and a bulk sample. The collection assembly includes a sample collection container having an opening and a drop sample substrate positioned across the opening and capable of being puncturable by a probe. The substrate includes a drop sample retaining surface facing the container interior for retaining a drop sample upon withdrawal of the probe from the container.

The container preferably includes an interior and exterior surface. The drop sample substrate is in the shape of an elongate strip having a first portion attached to the exterior surface of the container and a second portion positioned across the opening of the container. The second portion of the elongate strip is removable from the first portion by way of a perforation therebetween.

The interior surface of the drop sample substrate may include a specimen retaining filter paper for containing the specimen upon withdrawal of the probe.

The drop sample substrate may further include a specimen impervious liner surface opposite the sample retaining surface. The liner surface helps prevent fluid leakage therethrough.

The elongate strip may include indicia bearing locations in both the first and second portions. These indicia bearing locations provide coordinated identification of the bulk sample and the drop sample where the drop sample is transported separately from the bulk sample.

The container may be covered by a container closure over the opening, whereby the drop sample substrate is positionable over the closure.

The present invention may be used to collect a bulk specimen which is defined to be a quantity of a certain biological specimen such as blood, urine, saliva, sputum or fecal samples larger than a few drops. The present invention further provides for collection of a drop sample which is defined to be a small quantity, such as a single drop, on a substrate simultaneously with the collection of the bulk sample.

The present invention provides a sample collection assembly for creating a drop sample simultaneously with collection of a bulk sample. The present invention further provides for identification of the bulk sample and the drop sample for permitting coordinated tracking of the bulk sample and drop sample during transportation and testing.

The assembly of the present invention provides the means to separate and trap formed elements such as cells, virus, platelets and bacteria from the fluid portion of a biological sample, thus eliminating sample preparation steps such as centrifugation, filtration or precipitation.

Another attribute of the assembly of the present invention is that it provides for transport of a non-liquid sample as well as provides a stable sample for laboratory analysis.

DETAILED DESCRIPTION

Figure 1:
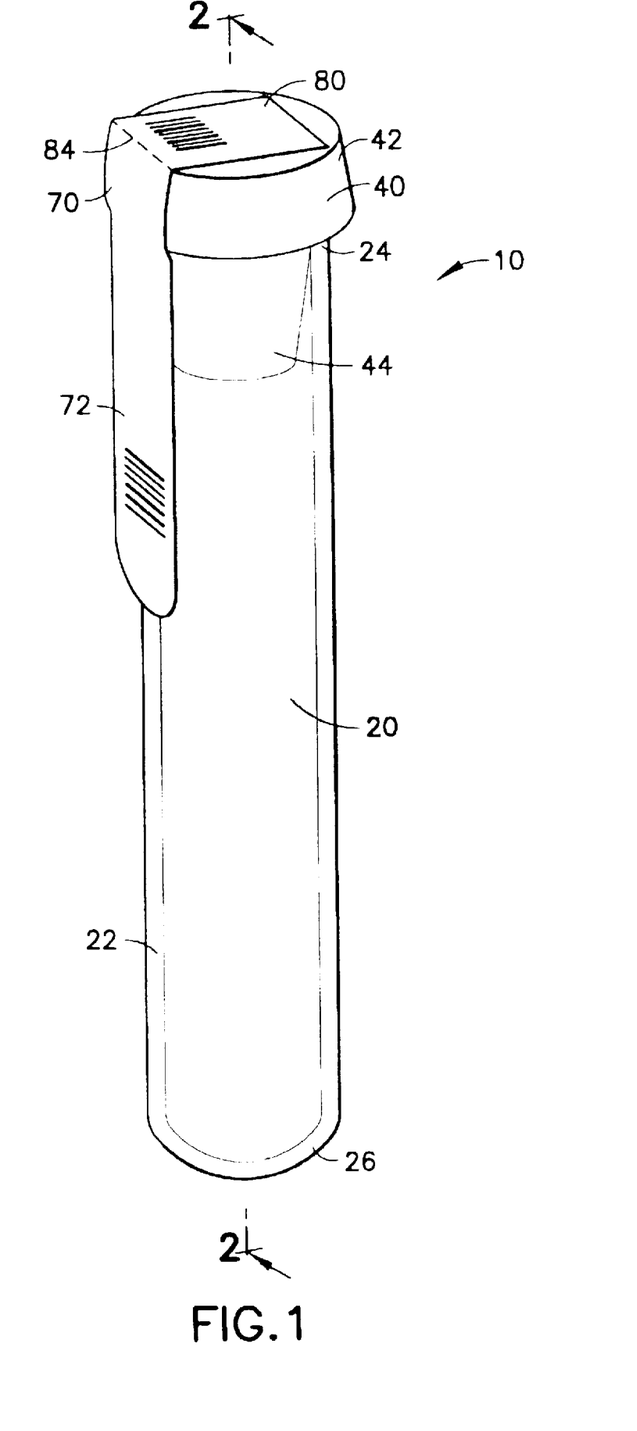
FIG. 1 is a perspective view of a sample collection assembly of the present invention.
Figure 2:
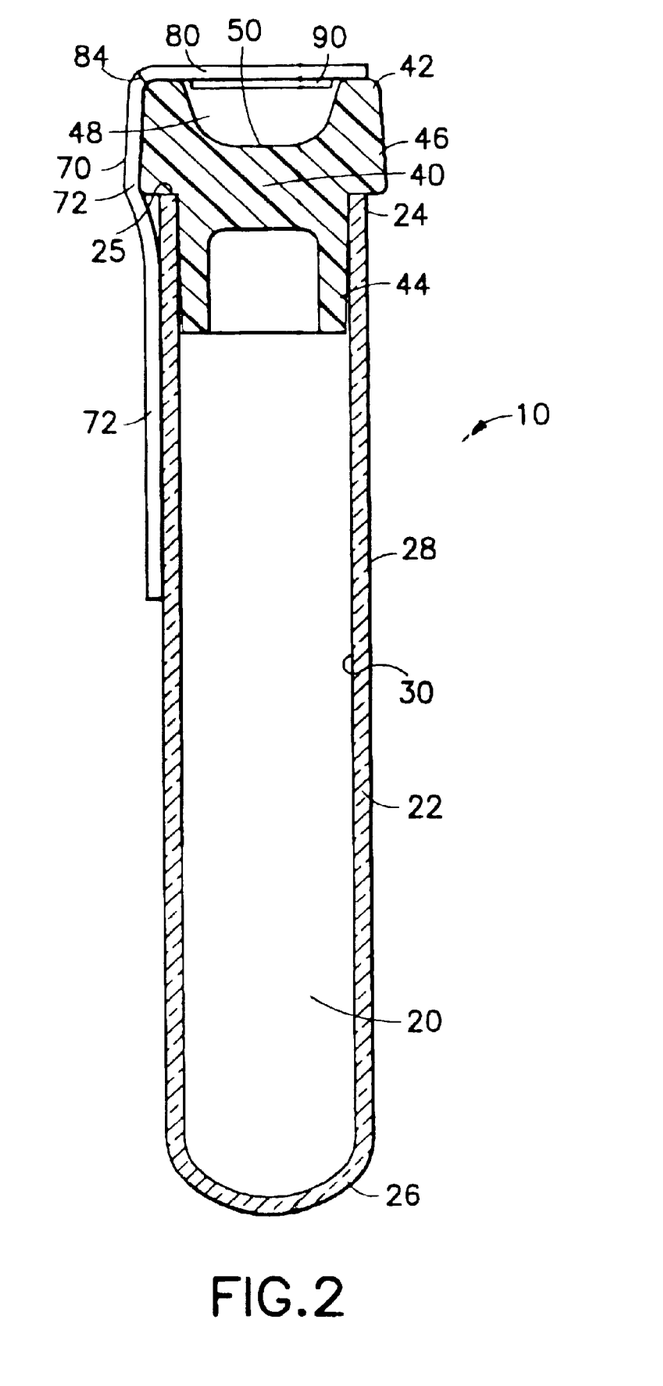
FIG. 2 is a longitudinal sectional view of the assembly of FIG. 1 taken along line 2—2 thereof.

Referring to the drawings in which the like reference characters refer to like parts throughout the several views thereof, FIGS. 1 and 2 illustrate the sample collection assembly 10 of the present invention. Collection assembly 10 includes a specimen collection container 20, a closure 40, and a drop sample collection substrate strip 70. Drop sample collection substrate 70 is attached to container 20 and positioned over closure 40. Container 20 includes a sidewall 22 extending from an open end 24 to a closed end 26. Sidewall 22 includes an exterior wall surface 28 and an interior wall surface 30 and open end 24 includes a top edge 25.

As shown below in FIGS. 1 and 2, closure 40 includes an annular upper portion 42 and a depending lower annular skirt 44. Lower skirt 44 is dimensioned to fit within open end 24 of container 20 to provide an interference fit with interior wall surface 30 of sidewall 22 of container 20. Upper annular portion 42 extends over top edge 25 of open end 24 to provide a sealed engagement therewith.

Annular upper portion 42 of closure 40 includes an upper annular rim surface 46 and a concave well 48. A central portion 50 of well 48 defines a self-sealing septum. The material forming the self-sealing septum allows pierceable insertion of a probe therethrough for depositing a sample within the interior of container 20 and also provides for self sealing upon withdrawal of a probe therefrom. Closure 40 of the present invention is preferably made of resilient elastomeric material such as natural rubber, synthetic thermoplastic or a sufficiently resilient thermoset material.

As shown in FIGS. 1 and 2, strip 70 is an elongate planar member which may be formed of a wide variety of materials including paper, plastic and the like and combinations thereof Strip 70 or portions thereof may be formed of liquid impervious materials to prevent sample leakage or bleeding therethrough. Strip 70 extends over closure 40 across well 48.

Strip 70 includes a first portion 72 which extends along an exterior wall surface 28 of container 20 adjacent open end 24. First portion 72 may be adhered to exterior wall surface 28 by, for example, a releasable adhesive. When used with closure 40, first portion of strip 72 extends over upper annular portion 42 of closure 40.

Strip 70 further includes an integrally formed second portion 80 which extends over upper annular rim surface 46 of closure 40 to overlie and cover well 48. Second portion 80 of strip 70 may be adhesively secured to upper annular rim surface 46 by a releasable adhesive.

Strip 70 is integrally formed, with second portion 80 being removably separable from first portion 72. Preferably, such removable separation is provided by a perforation line 84 extending therebetween.

Figure 3:
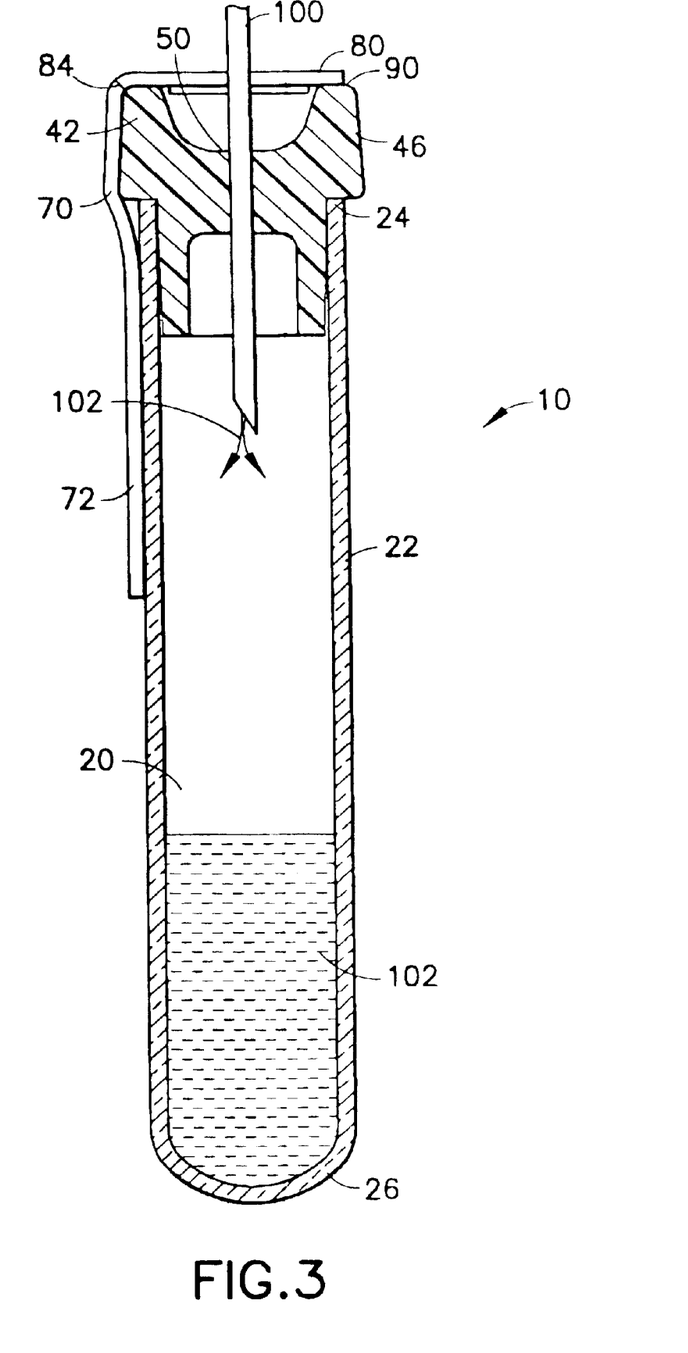
FIG. 3 is a sectional showing of the assembly of FIG. 2 illustrating delivery of a sample via an inserted probe.
Figure 4:
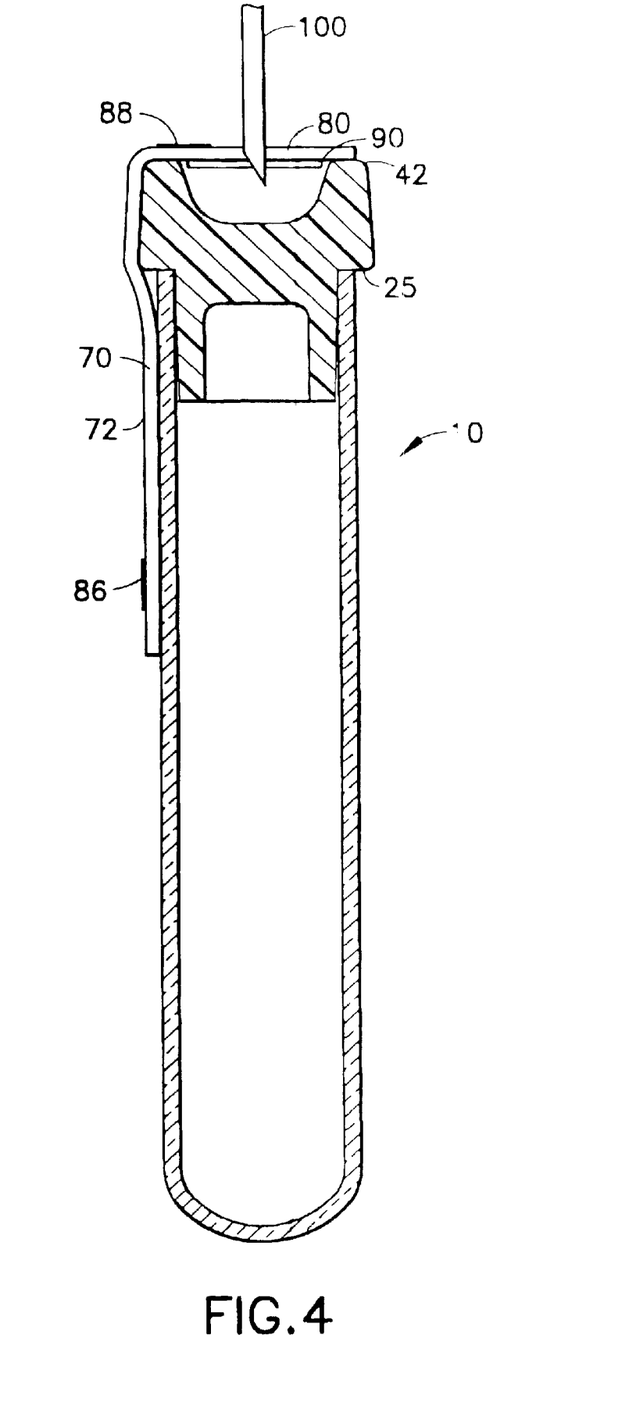
FIG. 4 is a sectional showing of the assembly of FIG. 2 illustrating the collection of a drop sample upon probe withdrawal.
Figure 5:
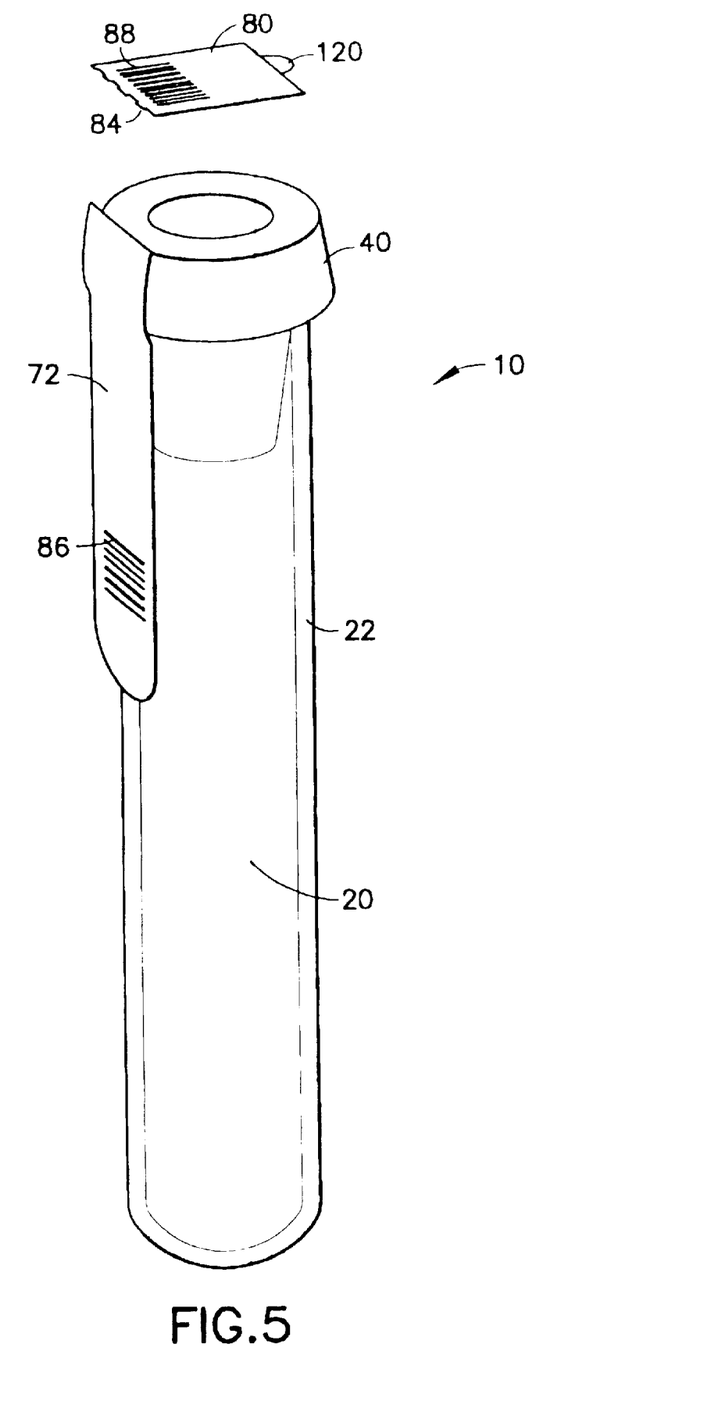
FIG. 5 is a perspective view of the sample collection assembly of FIG. 1 with a portion of the drop sample substrate removed therefrom.

As shown in FIGS. 4 and 5, first portion 72 of strip 70 may include an indicia bearing location 86 thereon. An indicia bearing location 88 may also be located on second portion 80 of strip 70. Indicia bearing locations 86 and 88 may contain identical indicia which would provide identification information such as information related to the patient from whom the sample is taken, the type of sample taken, the date of the sample and any other identification deemed necessary to provide proper identification and tracking of the sample. Such indicia may be provided by alphanumeric indication and/or may include other identifying mechanisms such as bar and/or color coding. It is desirable to provide identical indicia on both first portion 72 and second portion 80 of strip 70 so that when second portion 80 is removed from first portion 72 at perforation line 84, identification and tracking of the sample is provided Preferably, the undersurface of second portion 80 of strip 70 may include a sample retaining liner 90. Liner 90, as shown in FIGS. 2–3 may be pretreated filter paper which may contain stabilizers, decontaminants or sample dilution systems for PCR or other gene amplication analyses. Liner 90 which may be adhesively secured to the undersurface of second portion 80.

As shown in FIG. 3–5, a sample probe 100 is inserted into container 20 so as to deposit a sample 102 into the container. Upon insertion, probe 100 passes through second portion 80 of strip 70 and then through central portion 50 of well 48 of closure 40. Probe 100 may be a hypodermic needle, a blood collection needle or any type of piercing element. Upon insertion of probe 100 into container 20, sample 102 is deposited. After a sufficient bulk of sample 102 is deposited within container 20, the probe is withdrawn from container 20. Upon withdrawal, a drop sample is deposited on the liner 90 of strip 70. Probe 100 is then completely withdrawn leaving a drop sample on liner 90 of second portion 80 of strip 70 and bulk sample 102 within container 20.

In order to provide for the separate transport of the drop sample from bulk sample 102, second portion 80 of strip 70 may be removed from first portion 72 by frangible removal at perforation line 84. Second portion 80 may include an extending tab 120 to help facilitate manual removal of second portion 80 from first portion 72. Second portion 80, including the drop sample, may then be transported separately from bulk sample 102 contained in container 20 for appropriate tests to be separately conducted on both drop sample 106 and bulk sample 102. Since first portion 72 of strip 70 is retained on container 20 and as first portion 72 and second portion 80 include identical identifying indicia at locations 86 and 88, identification correspondence is maintained between the bulk sample and the drop sample during their separate shipping for test purposes.

Figure 6:
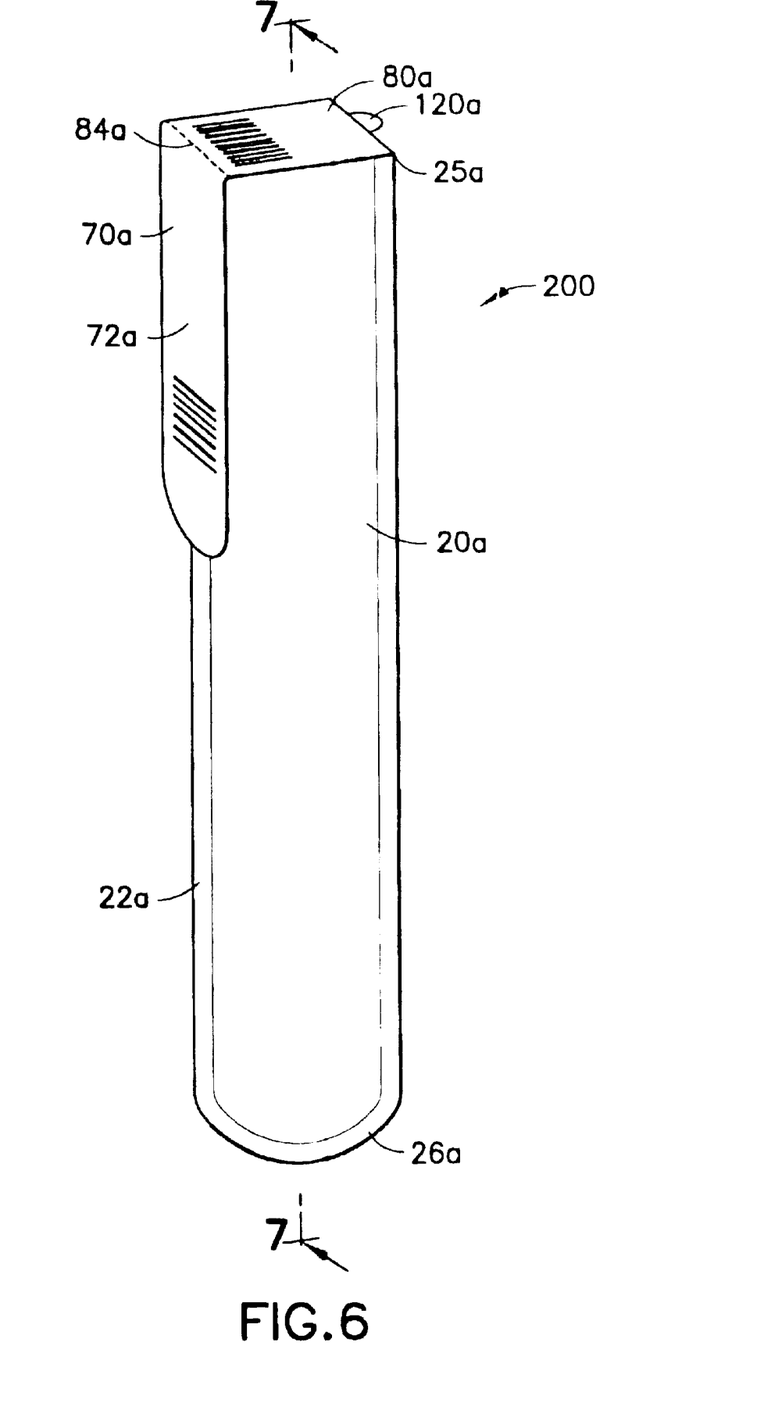
FIG. 6 is a perspective view of an alternative sample collection assembly of the present invention.
Figure 7:
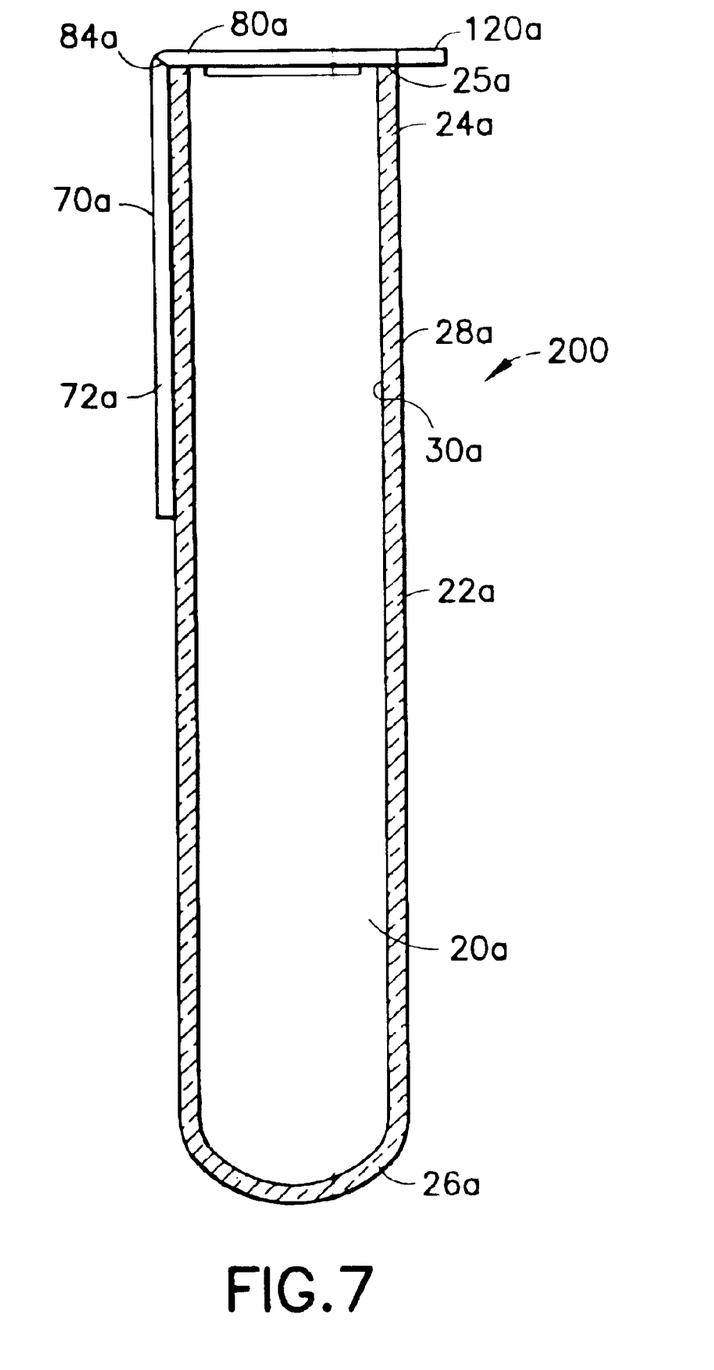
FIG. 7 is a longitudinal sectional view of the assembly of FIG. 6 taken along line 7—7 thereof.

FIGS. 6–7 illustrate an alternative embodiment of the present invention that may include components which are substantially identical to the components of FIGS. 1–5. Accordingly, similar components performing similar functions will be numbered identically to those components of FIGS. 1–5, except that a suffix "a" will be used to identify those similar components in FIGS. 6–7.

Alternatively, as shown in FIGS. 6–7, the sample collection assembly 200 may not have a closure and strip 70a may be positioned over open end 24a of container 20a.

For purposes of illustration, second portion 80a of strip 70a extends over and across open end 24a of container 20a and second portion 80a may be adhesively secured to top edge 25a of container 20a by a releasable adhesive.

It is contemplated that the embodiments of the present invention may be employed in combination with a mailer, or other transporting device to permit the dry stable drop sample to be safely shipped to a test location.

What is claimed is:

1. An assembly for collection of a drop sample comprising:
    a sample collection container having an opening and a container interior for collection of a bulk sample from a probe withdrawably insertable through said opening; and
    a drop sample substrate positioned across said opening and being puncturable by said probe, said substrate including a drop sample retaining surface facing said container interior for retaining said drop sample upon withdrawal of said probe from said container.

2. The assembly of claim 1, wherein said container includes an interior and exterior wall surface and wherein said substrate is an elongate strip having a first portion attached to said exterior wall surface of said container and a second portion positioned across said opening.

3. The assembly of claim 1, wherein said second portion of said strip is removable from said first portion.

4. The assembly of claim 3, wherein said first and second portions are separated by a perforation.

5. The assembly of claim 1, wherein said substrate further includes a specimen impervious surface opposite said sample retaining surface.

6. The assembly of claim 1, wherein said drop sample retaining surface includes specimen retaining liner.

7. The assembly of claim 6, wherein said liner includes a pre-treated filter paper.

8. The assembly of claim 3, wherein said elongate strip includes indicia bearing locations on said first and second portions for providing coordinated identification of said bulk sample and said drop sample.

9. The assembly of claim 1, further including a container closure positionable in sealed relationship within said opening, said closure being puncturable by said probe and said drop sample substrate being positionable over said closure.

10. The assembly of claim 9, wherein said closure includes an upper surface and a central well area, said well area defining a puncturable portion of said closure.

11. The assembly of claim 10, wherein said drop sample substrate is adhered to said upper surface of said closure.

12. An assembly for the simultaneous collection of a bulk specimen sample and a drop specimen sample comprising:

an open ended collection container for accommodating said bulk specimen deposited by a probe inserted through said open end; and a drop specimen collection substrate positioned across said open end for engagement with said probe so as to collect said drop specimen upon withdrawal of said probe from said container.

13. The assembly of claim 12, wherein said drop specimen collection substrate includes a drop specimen retaining surface.

14. The assembly of claim 13, wherein said drop specimen collection substrate includes a strip, said strip having a first portion attached to said container and a second portion secured across said open end of said container.

15. The assembly of claim 14, wherein said second portion of said strip is detachable from said first portion of said strip.

16. The assembly of claim 15, wherein said first and second portions of said strip include coordinated identifying indicia.

* * * * *